United States Patent [19]

Hirai et al.

[11] Patent Number: 4,546,094
[45] Date of Patent: Oct. 8, 1985

[54] SOLID ADSORBENT FOR UNSATURATED HYDROCARBON AND PROCESS FOR SEPARATION OF UNSATURATED HYDROCARBON FROM GAS MIXTURE

[75] Inventors: Hidefumi Hirai, 14-10, Yutenji 1-chome, Meguro-ku, Tokyo; Makoto Komiyama; Susumu Hara, both of Tokyo, all of Japan

[73] Assignee: Hidefumi Hirai, Tokyo, Japan

[21] Appl. No.: 587,657

[22] Filed: Mar. 8, 1984

[30] Foreign Application Priority Data

| Mar. 16, 1983 | [JP] | Japan | 58-043650 |
| Apr. 27, 1983 | [JP] | Japan | 58-074691 |
| May 18, 1983 | [JP] | Japan | 58-086949 |
| Jan. 7, 1984 | [JP] | Japan | 59-001161 |
| Jan. 7, 1984 | [JP] | Japan | 59-001162 |
| Jan. 7, 1984 | [JP] | Japan | 59-001163 |

[51] Int. Cl.$^4$ .................. B01J 20/26; B01D 53/02; C07C 7/12
[52] U.S. Cl. ..................... 502/402; 55/74; 585/829
[58] Field of Search ................. 502/401–404, 502/407, 414

[56] References Cited

U.S. PATENT DOCUMENTS

| 2,401,114 | 5/1946 | Schultze et al. | 585/830 |
| 2,606,938 | 8/1952 | Robinson | 585/829 |
| 3,243,471 | 3/1966 | Sterm et al. | 502/407 |
| 3,399,513 | 9/1968 | House et al. | 585/829 |
| 3,651,159 | 3/1972 | Long et al. | 502/414 |

*Primary Examiner*—P. E. Konopka
*Attorney, Agent, or Firm*—Cushman, Darby & Cushman

[57] ABSTRACT

A solid adsorbent for an unsaturated hydrocarbon comprising (a) (i) a silver or copper(I) halide or (ii) a silver or copper(I) halide and the halide of a bivalent metal, or (iii) a silver or copper(I) halide and an aluminum halide, and (b) polystyrene or a derivative thereof.

This solid adsorbent can effectively adsorb an unsaturated hydrocarbon such as ethylene from a gas mixture by contacting the gas mixture therewith at a temperature of $-40°$ C. to $140°$ C. under normal pressures.

7 Claims, No Drawings

SOLID ADSORBENT FOR UNSATURATED HYDROCARBON AND PROCESS FOR SEPARATION OF UNSATURATED HYDROCARBON FROM GAS MIXTURE

BACKGROUND OF THE INVENTION

1. Field of the Invention

The present invention relates to a solid adsorbent for an unsaturated hydrocarbon such as ethylene, propylene, 1-butene, 2-butene, 1-pentene, 2-pentene, 1-hexene, 2-hexene, cyclopentene, cyclohexene, butadiene, pentadiene, hexadiene cyclopentadiene, and cyclohexadiene. The present invention also relates to a process for separating an unsaturated hydrocarbon from a gas mixture containing the same, together with nitrogen, oxygen, methane, ethane, carbon dioxide, and hydrogen.

2. Description of the Prior Art

Unsaturated hydrocarbons such as monoolefins (e.g., ethylene) and dienes are the most important basic or fundamental raw materials in the chemical industry. These unsaturated hydrocarbons are produced by the pyrolysis of saturated hydrocarbons such as natural gases, refinery gases, and petroleum fractions. Furthermore, substantial amounts of unsaturated hydrocarbons are contained in off gases derived, as by-products, from fluid catalytic cracking and also in purge gases derived from various processes. These gases, however, contain unsaturated hydrocarbons together with nitrogen, oxygen, methane, ethane, carbon monoxide, carbon dioxide, and hydrogen. Furthermore, these gases contain 1000 to 20000 ppm of water. Accordingly, the unsaturated hydrocarbons must be separated from these gas mixtures in order to use the unsaturated hydrocarbons as raw materials for chemical synthesis.

Known processes for separating unsaturated hydrocarbons from gas mixtures include a so-called cryogenic gas separation process. In this process, a gas mixture is liquefied by cooling and is then fractionated at an extremely low temperature (e.g., $-95°$ C. to $-140°$ C., in the case of ethylene). However, this process also has disadvantages in that complicated refrigeration and heat recovery systems are required, the equipment is expensive due to the use of high-grade materials, the power consumption is large, and the separation of carbon monoxide and nitrogen is difficult. In addition, water and carbon dioxide contained in the gas mixture must be removed from the gas mixture in a pre-treatment apparatus so that the content thereof is less than 1 ppm, since clogging will occur in a low-temperature pipe line system when water and carbon dioxide are contained in the gas mixture.

U.S. Pat. No. 3,651,159 discloses that a toluene solution of aluminum copper(I) chloride $CuAlCl_4$ can separate an unsaturated hydrocarbon such as ethylene from a gas mixture containing the same, by forming a complex with the unsaturated hydrocarbon. This process, however, has disadvantages in that, since the aluminum copper(I) chloride is strongly reacted with water to irreversibly lose its complex-forming capability, the separation capacity is gradually decreased with the increase in the gas treatment amount even where the gas mixture contains as low as 1 ppm of water, and the unsaturated hydrocarbon separation apparatus is corroded due to the hydrogen chloride derived from the reaction of the aluminum copper(I) chloride with water. This process has further disadvantages in that toluene vapor must be separated from the recovered unsaturated hydrocarbon in a separate step, since the recovered unsaturated hydrocarbon released from the toluene solution of the aluminum copper(I) chloride contains the vapor of the toluene solvent, and that the process using a liquid absorbent is disadvantageous when compared with the process using a solid absorbent, from the viewpoints of the various process limitations. Furthermore, since the absorbed solution contains aluminum chloride therein, a Friedel-Crafts reaction of the unsaturated hydrocarbon with toluene in the presence of the aluminum chloride catalyst occurs, as a side reaction, causing a loss of the unsaturated hydrocarbon and denation of the liquid absorbent.

Other various processes for separating unsaturated hydrocarbons from gas mixtures have been proposed. However, until now there has been no satisfactory process in the art for separating unsaturated hydrocarbons from gas mixtures, especially by using solid adsorbents.

SUMMARY OF THE INVENTION

Accordingly, the objects of the present invention are to eliminate the above-mentioned disadvantages of the prior arts and to provide a solid adsorbent which is capable of adsorbing and releasing an unsaturated hydrocarbon under relatively mild conditions.

Another object of the present invention is to provide a process for effectively separating an unsaturated hydrocarbon from a gas mixture in which the unsaturated hydrocarbon can be effectively and economically adsorbed and released.

Other objects and advantages of the present invention will be apparent from the description set forth hereinbelow.

In accordance with the present invention, there is provided a solid adsorbent for an unsaturated hydrocarbon comprising (a)(i) a silver or copper(I) halide, (ii) a silver or copper(I) halide and the halide of a bivalent metal or (iii) a silver or copper (I) halide and aluminum halides, and (b) polystyrene or a derivative thereof.

In accordance with the present invention, there is also provided a process for separating an unsaturated hydrocarbon from a gas mixture containing the same comprising the step of:

contacting the gas mixture with a solid absorbent comprising (a)(i) a silver or copper(I) halide, (ii) a silver or copper(I) halide and the halide of a bivalent metal, or (iii) a silver or copper(I) halide and an aluminum halide and (b) polystyrene or a derivative thereof.

DESCRIPTION OF THE PREFERRED EMBODIMENTS

The solid adsorbent for an unsaturated hydrocarbon according to the present invention can be prepared by mixing (a)(i) a silver or copper(I) halide, (ii) a silver or copper(I) halide and the halides of bivalent metals, or (iii) a silver or copper(I) halide and an aluminum halide and (b) polystyrene or a derivative thereof in a solvent, while stirring, and then evaporating the solvent from the mixture.

Examples of the silver halides usable in the present invention are silver chloride, silver bromide, and silver iodide. These halides can be used alone or in any mixtures thereof.

Examples of the copper(I) halides usable in the present invention are copper(I) chloride, copper(I) bromide, and copper(I) iodide. These halides can be used alone or in any mixtures thereof.

Examples of the halides of bivalent metals usable in the present invention are calucium chloride and magnesium chloride.

Examples of the aluminum halides usable in the present invention are aluminum chloride, aluminum fluoride, aluminum bromide, and aluminum iodide.

The polystyrene or its derivatives (i.e., the component (b)) usable in the present invention include, for example, any conventional polystyrene desirably having a number-average molecular weight of 5000 to 500,000 or styrene copolymers containing, as a comonomer, divinylbenzene, butadiene, or their derivatives. The desirable polystyrene derivatives are copolymers of 40 mol % to 99 mol %, preferably 60 mol % to 99 mol % of styrene, and 1 mol % to 60 mol %, preferably 1 mol % to 40 mol % of divinylbenzene. These polymers can be used alone or in any mixture thereof.

A molar ratio of the monomer residual group of the polystyrene or its derivatives to the silver or copper(I) halide in the solid adsorbent of the present invention is preferably 0.1 to 30, more preferably 1 to 5. The term "monomer residual group" used herein means a monomer unit incorporated into polymers or copolymers. A molar ratio of the monomer residual group of the polystyrene or its derivatives to the silver or copper(I) halide of less than 0.1 tends to decrease the unsaturated hydrocarbon capacity per silver or copper(I) halide in a solid adsorbent comprising (a)(i) a silver or copper(I) halide or (ii) a silver or copper(I) halide and the halides of bivalent metals and (b) polystyrene or the derivatives thereof. In a solid adsorbent comprising (a)(iii) silver or copper(I) halide and aluminum halides and (b) polystyrene or the derivative thereof, a molar ratio of the monomer residual group of the polystyrene or its derivatives to the silver or copper(I) halide of less than 0.1 tends to decrease the resistance of the adsorbent against water. Contrary to this, a molar ratio of more than 30 tends to decrease the unsaturated hydrocarbon capacity per unit volume of the adsorbents.

A molar ratio of (1) at least one member selected from the group consisting of the halides of bivalent metals, and aluminum halides to (2) the silver or copper(I) halide contained in the component (a)(ii) of the present adsorbent is preferably 0.1 to 10, more preferably 0.5 to 10, and most preferably 1.0 to 2.0. A molar ratio of less than 0.1 tends to decrease the unsaturated hydrocarbon capacity per silver or copper(I) halide. Contrary to this, a molar ratio of more than 10 tends to decrease the unsaturated hydroxarbon capacity per unit weight of the adsorbent.

The solvents usable for the preparation of a solid adsorbent comprising (a)(i) silver or copper(I) halide or (ii) silver or copper(I) halide and the halides of bivalent metals and (b) polystyrene or the derivative thereof are, for example, carbon disulfide, dichloromethane, chloroform, tetrachloromethane, dichloroethane, trichloroethane, tetrachloroethane, benzene, toluene, xylene, chlorobenzene, cyclohexane, decalin, acetonitrile, propionitrile, acetone, methyl isobutyl ketone, ethyl acetate, water, an aqueous hydrogen halide (e.g., HCl, HBr) solution, methanol, ethanol, and isopropanol. The solvents usable for the preparation of a solid adsorbent comprising (a)(iii) silver or copper (I) halide and aluminum halides and (b) polystyrene or the derivative thereof are, for example, carbon disulfide, dichloromethane, chloroform, tetrachloromethane, dichloroethane, trichloroethane, tetrachloroethane, benzene, toluene, xylene, chlorobenzene, cyclohexane, and decalin.

As mentioned above, the present solid adsorbents can be prepared by mixing the above-mentioned components together at a temperature of, for example, 10° C. to 100° C., desirably 20° C. to 60° C. for one minute to 10 hours, preferably 1 to 3 hours, while stirring in a solvent under an inert atmosphere of, for example, nitrogen, helium, or argon, and then removing the solvent by, for example, reduced distillation (e.g., at a temperature of 0° C. to 250° C., preferably 10° C. to 180° C., under an absolute pressure of $10^{-6}$ mmHg to $10^2$ mmHg, preferably $10^{-2}$ mmHg to 10 mmHg).

The unsaturated hydrocarbons which can be separately adsorbed by the present adsorbents are monoolefins having 2 to 15 carbon atoms (e.g., ethylene, propylene, 1-butene, 2-butene, 1-pentene, 2-pentene, 1-hexene, 2-hexene cyclo-pentene, and cyclohexene), and dienes (e.g., butadiene, pentadiene, hexadiene, cyclopentadiene, and cyclohexadiene).

As illustrated in the examples given hereinbelow, the adsorbent of the present invention can effectively adsorb an unsaturated hydrocarbon contained in a gas mixture by contacting the gas mixture with the present adsorbent at a temperature of −40° C. to 140° C., preferably 0° C. to 40° C., under normal pressure (e.g., 1 atm). The unsaturated hydrocarbon adsorption can be also carried out under an elevated pressure. In this case, the adsorption can be carried out at a temperature of higher than 140° C.

The adsorbed unsaturated hydrocarbon is readily released or desorbed by heating the adsorbents at a temperature of 40° C. to 140° C., preferably 60° C. to 100° C. The desorption of the unsaturated hydrocarbon can be also readily carried out by evacuating the system containing the adsorbent or decreasing a partial pressure of the unsaturated hydrocarbon in the system containing the adsorbent.

The solid adsorbents of the present invention are inert and stable against the water and carbon dioxide possibly contained in the gas mixtures to be treated and, therefore, the desired unsaturated hydrocarbon can be directly separated from the gas mixture containing water (e.g., approximately 40,000 ppm by volume at 30° C. or less) without causing a substantial decrease in the adsorbing capacity of the unsaturated hydrocarbon after repeated use, as illustrated in the Examples hereinbelow. Furthermore, the present solid adsorbents do not catalyze a Friedel-Crafts reaction of the unsaturated hydrocarbons.

In particular, when the present solid adsorbents is prepared from a silver halide, an aluminum halide, and polystyrene or its derivative, the resultant solid adsorbents are inert against carbon monoxide, so that the desired unsaturated hydrocarbon (e.g., ethylene) is selectively separated from gas mixtures containing carbon monoxide.

The solid adsorbents of the present invention can be packed in a packed column, a packed tower, and a fluidized bed to adsorb and desorb unsaturated hydrocarbons.

EXAMPLES

The present invention will now be further illustrated by, but is by no means limited to, the following examples.

EXAMPLE 1

The following chemicals and gases were used in this example.

Aluminum chloride: Special grade chemical aluminum (III) chloride, manufactured by Kishida Kagaku Kogyo Kabushiki Kaisha (Japan), was purified by dewatering the same by means of a vacuum sublimation method.

Silver chloride: Special grade chemical silver halide, manufactured by Kojima Yakuhin Kabushiki Kaisha (Japan).

Carbon disulfide: First grade chemical carbon disulfide, manufactured by Yoneyama Yakuhin Kogyo Kabushiki Kaisha (Japan), was dewatered over phosphorus pentoxide, followed by distillation.

Polystyrene resin: Bio-Beads SM-2 (copolymer beads of 80 mol % styrene and 20 mol % divinylbenzene having a size of 20 to 50 mesh manufactured by Bio-Rad Laboratories Co., Ltd.) were purified by washing the beads while stirring with a magnetic stirrer, in a 6N hydrochloric acid at 55° C. for 2 hours, in a 4N sodium hydroxide at 55° C. for 2 hours, in water at 55° C. for 2 hours, in methanol at 25° C. for 1 hour, and in a dichloromethane at 25° C. for 1 hour, to remove impurities from the beads, and then vacuum dried at 100° C. for 12 hours.

Ethylene gas: A bomb gas manufactured by Takachiho Kagaku Kabushiki Kaisha (Japan) was used after adjusting the water content to 0.6 mol % (i.e., 6000 ppm).

Carbon monoxide: A bomb gas (purity: 99.95%), manufactured by Takachiho Kagaku Kabushiki Kaisha (Japan), was dried and purified by passing the gas through a column packed with molecular sieve 3A (Nikka Seiko Kabushiki Kaisha, Japan) just before use.

Nitrogen: A bomb gas (purity: 99.999%), obtained from Kabushiki Kaisha Suzuki Shokan (Japan), was dried and purified by passing the gas through a column packed with molecular sieve 3A (Nikka Seiko Kabushiki Kaisha, Japan) just before use.

Into a 100 mol two-necked, eggplant-type flask covered with aluminum foil, 3.10 g (23.3 mmol) of aluminum chloride, 3.33 g (23.3 mmol) of silver chloride, and 5.07 g (46.5 mmol in terms of the monomer residual group) of crosslinked polystyrene resin, Bio-beads SM-2, were charged under a dry nitrogen atmosphere. A 20 ml amount of carbon disulfide was added to the mixture. The mixture was heated under reflux while being stirred with a magnetic stirrer. Thereafter, the carbon disulfide was thoroughly removed by evacuating the flask to 4 mmHg while stirring with a magnetic stirrer at a temperature of 20° C. to 50° C. for 6 hours. Thus, a solid adsorbent in the form of pale red-brown resin particles was prepared.

The adsorbent was charged into a 100 mol two-necked, eggplant-type flask and ethylene gas was then adsorbed onto the adsorbent at 20° C. by connecting the flask to a vessel containing the ethylene gas (water content=0.6 mol %) at 1 atm, while the adsorbent was stirred with a magnetic stirrer.

The ethylene was rapidly adsorbed onto the adsorbent. That is, 15.2 mmol (65 mol % of the charge silver halide) of ethylene was adsorbed after 5 minutes, 20.3 mmol (87 mol % of the charged silver halide) after 30 minutes, and 23,5 mmol (101 mol % of the charged silver halide) after 120 minutes. The ethylene adsorbed adsorbent was then evacuated to 8 mmHg at 20° C. for 10 minutes by connecting the two-necked flask with a vacuum pump. Thus, the adsorbed ethylene was released from the adsorbent.

Thereafter, ethylene was adsorbed onto the adsorbent at 20° C. by connecting the two-necked flask to the vessel containing the ethylene gas (water content=0.6 mol %) at 1 atm, while the adsorbent was stirred with a magnetic stirrer.

The ethylene was rapidly adsorbed onto the adsorbent. That is, 16.7 mmol (72 mol % of the charged silver halide) of ethylene was adsorbed after 4 minutes and 22.7 mmol (98 mol % of the charged silver halide) of ethylene after 120 minutes. The ethylene adsorbed adsorbent was then evacuated to 8 mmHg at 20° C. for 10 minutes by connecting the two-necked flask with a vacuum pump. Thus, adsorbed ethylene was released from the adsorbent.

Thereafter, ethylene was again adsorbed onto the adsorbent contained in the two-necked flask at 20° C. by connecting the two-necked flask to the vessel containing the ethylene gas (water content=0.6 mol %) at 1 atm, while the adsorbent was stirred with a magnetic stirrer.

The ethylene was rapidly adsorbed onto the adsorbent. That is, 19.5 mmol (84 mol % of the charged silver chloride) of ethylene was adsorbed after 5 minutes and 22.5 mmol (97 mol % of the charged silver chloride) of ethylene after 120 minutes. The ethylene adsorbed adsorbent was evacuated to 8 mmHg at 20° C. for 10 minutes by connecting the two-necked flask with a vacuum pump, and then the two-necked flask was connected at 20° C. to a vessel containing a carbon monoxide gas at 1 atm. However, no carbon monoxide was adsorbed onto the adsorbent. Thereafter, the two-necked flask was evacuated at 20° C. to 8 mmHg for 10 minutes with a vacuum pump and ethylene was then adsorbed onto the adsorbent contained in the two-necked flask at 20° C. by contacting the adsorbent with the ethylene gas (water content=0.6 mol %) at 1 atm. The ethylene was rapidly adsorbed onto the adsorbent. That is, 24.5 mmol (105 mol % of the charged silver chloride) of ethylene was adsorbed onto the adsorbent.

As is clear from the above results, the ethylene adsorption capacity of the present solid adsorbent was not substantially changed after the adsorption of the ethylene gas containing 0.6 mol % of water was repeated 5 times. Furthermore, no carbon monoxide was adsorbed onto the present solid adsorbent.

EXAMPLE 2

The chemicals and gases used in Example 1 were used.

Into a 100 ml two-necked, eggplant-type flask covered with aluminum foil, 2.2 g (17.2 mmol) of aluminum chloride, 2.46 g (17.2 mmol) of silver chloride, and 2.25 g (21.6 mmol in terms of the monomer residual group) of polystyrene resin, Bio-Beads SM-2, were charged under a dry nitrogen atmosphere. A 10 ml amount of carbon disulfide was added to the mixture. The mixture was heated under reflux while being stirred with a magnetic stirrer. Thereafter, the carbon disulfide was thoroughly removed by evacuating the flask to 4 mmHg while stirring with a magnetic stirrer at 20° C. to 50° C. for 6 hours. Thus, a solid adsorbent was prepared.

The adsorbent was charged into a 100 ml two-necked, eggplant-type flask and then an ethylene gas was adsorbed onto the adsorbent at 22° C. by connecting the flask to a vessel containing the ethylene gas (water content=0.6 mol %) at 1 atm, while the adsorbent was stirred with a magnetic stirrer.

The ethylene was rapidly adsorbed onto the adsorbent. That is, 12.3 mmol (72 mol % of the charged silver chloride) of ethylene was adsorbed after 5 minutes, 16.9 mmol (99 mol % of the charged silver chloride) after 30 minutes, and 18.7 mmol (109 mol % of the charged silver halide) after 60 minutes. The two-necked flask was heated in an oil bath at 1 atm to release 11.6 mmol (67 mol % of the charged silver halide) of ethylene at 70° C. for 2 minutes and 15.7 mmol (92 mol % of the charged silver halide) of ethylene at 100° C. for 2 minutes.

EXAMPLE 3

The chemicals and gases used in Example 1 were used except that first grade chemical toluene, manufactured by Takahashi Tokichi Shoten (Japan) was used instead of the carbon disulfide. The chemical toluene was dehydrated with sodium metal, followed by distillation.

Into a 100 ml two-necked, eggplant-type flask covered with aluminum foil, 3.53 g (26.5 mmol) of aluminum chloride, 3.80 g (26.5 mmol) of silver chloride, and 3.31 g (31.8 mmol in terms of the monomer residual group) of polystyrene resin, Bio-Beads SM-2, were charged under a dry nitrogen atmosphere. A 15 ml amount of toluene was added to the mixture. The mixture was heated at a temperature of 60° C. while being stirred with a magnetic stirrer. Thereafter, toluene was thoroughly removed by evacuating the flask to 4 mmHg while stirring with a magnetic stirrer at 20° C. to 65° C. for 6 hours. Thus, a solid adsorbent was prepared.

The adsorbent was charged into a 100 ml two-necked, eggplant-type flask and was then connected to a vessel containing carbon monoxide gas at 1 atm. Thus, the solid adsorbent was contacted with carbon monoxide at 25° C., while the adsorbent was stirred with a magnetic stirrer. However, no carbon monoxide (0 mmol) was adsorbed onto the adsorbent even after 120 minutes.

Thereafter, ethylene was adsorbed onto the adsorbent at 20° C. by connecting the flask to a vessel containing the ethylene gas (water content=0.6 mol %) at 1 atm, while the adsorbent was stirred with a magnetic stirrer.

As a result, the ethylene was rapidly adsorbed onto the adsorbent. That is, 21.4 mmol (81 mol % of the charged silver chloride) of ethylene was adsorbed after 5 minutes and 26.2 mmol (99 mol % of the charged silver chloride) of ethylene after 120 minutes.

EXAMPLE 4

The chemicals and gases used in Example 1 were used, except that special grade chemical toluene, manufactured by Takahashi Tokichi Shoten (Japan) was used instead of the carbon disulfide. The chemical toluene was dehydrated with sodium metal, followed by distillation.

Into a 100 ml two-necked, eggplant-type flask, 2.8 g (21 mmol) of aluminum chloride, 3.7 g (26 mmol) of silver chloride, and 3.1 g (30 mmol in terms of the monomer residual group) of polystyrene resin, Bio-Beads SM-2, were charged under a dry nitrogen atmosphere. A 20 ml amount of toluene was added to the mixture. The mixture was heated under reflux while being stirred with a magnetic stirrer. Thereafter, toluene was thoroughly removed by evacuating the flask to 4 mmHg while stirring with a magnetic stirrer at 20° C. to 50° C. for 6 hours. Thus, a solid adsorbent was prepared.

The ethylene adsorption amount was determined in the same manner as in Example 1.

As a result, 12 mmol of ethylene was adsorbed onto the adsorbent after 3 minutes, and 21 mmol of ethylene after 60 minutes.

The ethylene adsorbed adsorbent thus obtained was heated at 100° C. under 1 atm to rapidly release the ethylene. The released ethylene amount was 21 mmol after 10 minutes. The released gas was analyzed by a gas chromatography (Porapack Q column having a length of 2 m at a column temperature of 60° C.), with the result that no components other than ethylene were detected in the release gas.

EXAMPLE 5

The chemicals and gases used in Example 1 were used, except that special grade chemical dichloromethane manufactured by Nakarai Kagaku Yakuhin Kabushiki Kaisha was used instead of carbon disulfide. The dischloromethane was dehydrated with phosphorus pentoxide, followed by distillation.

Into a 100 ml two-necked, eggplant-type flask, 3.1 g (23 mmol) of aluminum chloride, 3.3 g (23 mmol) of silver chloride and 2.9 g (28 mmol in terms of the monomer residual group) of polystyrene resin, Bio-Beads SM-2 were charged under a dry nitrogen atmosphere. A 30 ml amount of dichloromethane was added to the mixture and the mixture was heated under reflux while being stirred with a magnetic stirrer. Thereafter, dichloromethane was thoroughly removed by evacuating the flask to 4 mmHg, while being stirred by means of a magnetic stirrer at 20° C. to 50° C. for 6 hours. Thus, a solid adsorbent was prepared.

The ethylene adsorption amounts were determined in the same manner as in Example 1.

As a result, 11 mmol of ethylene was adsorbed onto the adsorbent after 3 minutes and 23 mmol of ethylene after 60 minutes.

The ethylene adsorbed absorbent thus obtained was heated at 100° C. under 1 atm to rapidly release the ethylene. The released amount of ethylene was 23 mmol after 10 minutes. The released gas was ethylene and no other component was detected by the gas chromatograph analysis as in Example 4.

EXAMPLE 6

The chemicals and gases used in Example 1 were used, except that special grade chemical silver fluoride (manufactured by Kojima Kagaku Yakuhin Kabushiki Kaisha) was used instead of silver chloride.

Into a 100 ml two-necked, eggplant-type flask, 2.7 g (20 mmol) of aluminum chloride, 2.5 g (20 mmol) of silver fluoride, and 2.5 g (24 mmol in terms of the monomer residual group) of polystyrene resin, Bio-Beads SM-2 were charged, and then, 20 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent was prepared.

The ethylene adsorption amounts of the adsorbent were determined in the same manner as in Example 1.

As a result, 3.1 mmol of ethylene was adsorbed onto the adsorbent after 3 minutes and 5.2 mmol after 60 minutes.

The ethylene adsorbed adsorbent was heated at 100° C. under 1 atm to rapidly release the ethylene. The released amount of ethylene was 5.0 mmol after 10 minutes. As a result of the gas chromatograph analysis as in Example 4, the released gas was found to be ethylene and no other component was detected in the released gas.

EXAMPLE 7

The chemicals and gases used in Example 1 were used, except that special grade chemical silver fluoride (manufactured by Kojima Kagaku Yakuhin Kabushiki Kaisha) was used instead of silver chloride and special grade chemical aluminum bromide (manufactured by Kishida Kagaku Kogyo Kabushiki Kaisha) was used instead of aluminum chloride.

Into a 100 ml two-necked, eggplant-type flask, 5.9 g (22 mmol) of aluminum bromide, 2.8 g (22 mmol) of silver fluoride, and 2.9 g (28 mmol in terms of the monomer residual group) of polystyrene resin, Bio-Beads SM-2 were charged, and then 20 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent was prepared.

The ethylene adsorption amounts of the adsorbent were determined in the same manner as in Example 1.

As a result, 6.3 mmol of ethylene was adsorbed onto the adsorbent after 3 minutes and 12 mmol after 60 minutes.

The ethylene adsorbed adsorbent was heated at 100° C. under 1 atm to rapidly release the ethylene. The released amount of ethylene was 12 mmol after 10 minutes. As a result of the gas chromatograph analysis as in Example 4, the released gas was found to be ethylene and no other component was detected in the released gas.

EXAMPLE 8

A solid adsorbent was prepared in the same manner as in Example 1 from 3.1 g (23 mmol) of aluminum chloride, 3.3 g (23 mmol) of silver chloride, 5.1 g (47 mmol in terms of the monomer residual group) of polystyrene resin, Bio-Beads SM-2, and 20 ml of carbon disulfide.

The adsorbent was charged into a 100 ml two-necked, eggplant-type flask and the flask was then connected to a vessel containing a gas mixture of 353 ml of ethylene and 487 ml of carbon monoxide (initial partial pressures of ethylene and carbon monoxide are 0.42 atm and 0.58 atm, respectively) while the adsorbent was stirred with a magnetic stirrer. The adsorbed amounts were determined at 20° C. according to a gas burette method.

The gas was rapidly adsorbed onto the adsorbent. That is, 246 ml of the gas was adsorbed after 3 minutes and 280 ml of the gas after 60 minutes, which was approximately equilibrium adsorption amount. As a result of gas chromatograph analysis of the resultant gas mixture in the vessel, 73 ml of ethylene and 487 ml of carbon monoxide remained in the vessel. That is, 280 ml (11.5 mmol, 49 mol % of the charged silver chloride) of ethylene was adsorbed onto the adsorbent, while no carbon monoxide was adsorbed.

The ethylene adsorbed adsorbent was heated at 100° C. under 1 atm to rapidly release the ethylene. The released amount of ethylene was 11.5 mmol (49 mol % of the charged silver chloride) after 10 minutes. As a result of the gas chromatograph analysis, the released gas was found to be ethylene and no other component was detected in the released gas.

EXAMPLE 9

The chemicals and gases used in Example 1 were used, except that crosslinked polystyrene resin "S-2001" (manufactured by Shoko Tsusho Kabushiki Kaisha, copolymer beads of 71% styrene and 29% divinylbenzene, bead diameter of about 3 mm) was used instead of the polystyrene resin, Bio-Beads SM-2.

Into a 100 ml two-necked, eggplant-type flask, 3.1 g (23 mmol) of aluminum chloride, 3.3 g (23 mmol) of silver chloride, and 2.9 g (28 mmol in terms of the monomer residual group) of polystyrene resin, "S-2001" were charged, and then, 30 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent was prepared.

The ethylene adsorption amounts of the adsorbent were determined in the same manner as in Example 1.

As a result, 18 mmol of ethylene was adsorbed onto the adsorbent after 3 minutes and 22 mmol after 60 minutes.

The ethylene adsorbed absorbent was heated at 100° C. under 1 atm to rapidly release the ethylene. The released amount of ethylene was 22 mmol after 10 minutes. As a result of the gas chromatograph analysis as in Example 4, the released gas was found to be ethylene and no other component was detected in the released gas.

EXAMPLE 10

The following chemicals and gases were used in this Example.

Copper(I) chloride: Special grade chemical copper(I) chloride, manufactured by Komune Kagaku Yakuhin Kabushiki Kaisha (Japan), was purified by means of re-precipitation, ethanol and ether washing, and vacuum drying at 80° C. for 12 hours.
Aluminum chloride: The same as used in Example 1.
Carbon disulfide: The same as used in Example 1.
Polystyrene resin: The same as used in Example 1.
Ethylene gas: The same as used in Example 1.
Nitrogen gas: The same as used in Example 1.

Into a 100 ml two-necked, eggplant-type flask, 2.88 g (21.6 mmol) of aluminum chloride, 2.14 g (21.6 mmol) of copper(I) chloride, and 2.83 g (26.0 mmol in terms of the monomer residual group) of polystyrene resin, Bio-Beads SM-2, were charged under a dry nitrogen atmosphere. 20 ml of carbon disulfide was added to the mixture. The mixture was heated under reflux, while being stirred with a magnetic stirrer. Thereafter, carbon disulfide was thoroughly removed by evacuating the flask to 4 mmHg while stirring with a magnetic stirrer at 20° C. to 50° C. for 6 hours. Thus, a solid adsorbent in the form of pale red-brown resin particles was prepared.

The adsorbent was charged into a 100 ml two-necked, eggplant-type flask and the flask was connected to a vessel containing the ethylene gas (water content=0.6 mol %) at 1 atm. Thus, the ethylene was adsorbed at 20° C. onto the adsorbent, while the adsorbent was stirred with a magnetic stirrer.

The ethylene was rapidly adsorbed onto the adsorbent. That is, 18.0 mmol (83 mol % of the charged copper(I) chloride) of ethylene was adsorbed after 3 minutes, 23.1 mmol (107 mol % of the charged copper(I) chloride) of ethylene after 30 minutes, and 24.4 mmol (113 mol % of the charged copper(I) chloride) of ethylene after 120 minutes. The adsorbed ethylene was desorbed by evacuating the flask to 8 mmHg at 20° C. for 10 minutes with a vacuum pump.

The two-necked eggplant-flask was then connected to a vessel containing the ethylene gas (water content=0.6 mol %) at 1 atm. Thus, the ethylene was adsorbed at 20° C. onto the adsorbent, while the adsorbent was stirred with a magnetic stirrer. The ethylene was rapidly adsorbed onto the adsorbent. That is, 3.4 mmol (16 mol % of the charged copper(I) chloride) of ethylene was adsorbed after 3 minutes and 5.2 mmol (24 mol % of the charged copper(I) chloride) of ethylene after 120 minutes. The adsorbed ethylene was desorbed by evacuating the flask to 8 mmHg at 20° C. for 10 minutes with a vacuum pump.

Thereafter, the two-necked eggplant flask was again connected to a vessel containing the ethylene gas (water content=0.6 mol %) at 1 atm. Thus, the ethylene was adsorbed at 20° C. onto the adsorbent, while the adsorbent was stirred with a magnetic stirrer. The ethylene was rapidly adsorbed onto the adsorbent. That is, 3.3 mmol (15 mol % of the charged copper(I) chloride) of ethylene was adsorbed after 3 minutes and 5.1 mmol (24 mol % of the charged copper(I) chloride) of ethylene after 120 minutes.

Furthermore, the adsorbent of the present invention was contacted with the ethylene gas containing 0.6 mol % of water a further 5 times, and the ethylene adsorption amounts were substantially the same as those of the second and third times mentioned above.

EXAMPLE 11

The chemicals, gases, and solid adsorbent used in Example 10 were used.

The solid adsorbent prepared in the same manner as in Example 10 was charged into a 100 ml two-necked eggplant-flask. The flask was connected to a vessel containing the ethylene gas (water content=0.6 mol %) at 1 atm. Thus, the ethylene was adsorbed at 20° C. onto the adsorbent, while the adsorbent was stirred with a magnetic stirrer.

The ethylene was rapidly adsorbed onto the adsorbent. That is, 24.4 mmol (113 mol % of the charged copper(I) chloride) of ethylene was adsorbed after 120 minutes. The adsorbed ethylene was then desorbed under 1 atm by heating the adsorbent by 1.0 mmol (5 mol % of the charged copper(I) chloride) at 57° C., 4.0 mmol (19 mol % of the charged copper(I) chloride) at 85° C., 5.9 mmol (28 mol % of the charged copper(I) chloride) at 100° C., 8.0 mmol (37 mol % of the charged copper(I) chloride) at 124° C., and 8.5 mmol (39 mol % of the charged copper(I) chloride) at 152° C.

Thereafter, the flask was cooled from 152° C. to 20° C., while the flask was evacuated to 8 mmHg. The adsorbent was then again contacted with the ethylene gas (water content=0.6 mol %) at 20° C. under 1 atm to adsorb the ethylene by 7.3 mmol (34 mol % of the charged copper(I) chloride) after 3 minutes and 11.1 mmol (51 mol % of the charged copper(I) chloride) after 120 minutes.

EXAMPLE 12

The chemicals and gases used in Example 10 were used.

Into a 100 ml two-necked, eggplant-type flask, 2.46 g (18.4 mmol) of aluminum chloride, 2.74 g (27.7 mmol) of copper(I) chloride, and 3.61 g (33.2 mmol in terms of the monomer residual group) of polystyrene resin, Bio-Beads SM-2, were charged under a dry nitrogen atmosphere. 20 ml of carbon disulfide was added to the mixture. The mixture was heated at a temperature of 20° C. to 50° C. for 6 hours while being stirred with a magnetic stirrer. Thereafter, the carbon disulfide was thoroughly removed by evacuating the flask to 4 mmHg, while stirring with a magnetic stirrer at room temperature for 6 hours. Thus, a solid adsorbent was prepared. This solid adsorbent was substantially the same as that prepared in Example 10, except that 1.5 times by mol of aluminum chloride based on copper(I) chloride was included in the adsorbent.

The adsorbent was charged into a 100 ml two-necked, eggplant-type flask and then ethylene was adsorbed into the adsorbent at 20° C. by connecting the flask to a vessel containing the ethylene gas (water content=0.6 mol %) at 1 atm, while the adsorbent was stirred with a magnetic stirrer.

The ethylene was rapidly adsorbed onto the adsorbent. That is, 9.7 mmol (35 mol % of the charged copper(I) chloride) of ethylene was adsorbed after 3 minutes and 12.6 mmol (46 mol % of the charged copper(I) chloride) after 120 minutes. The adsorbed ethylene was desorbed by evacuating the flask to 8 mmHg at 20° C. for 10 minutes with a vacuum pump.

Thereafter, the two-necked eggplant flask was again connected to a vessel containing the ethylene gas (water content=0.6 mol %) at 1 atm. Thus, the ethylene was adsorbed at 20° C. onto the adsorbent, while the adsorbent was stirred with a magnetic stirrer. The ethylene was rapidly adsorbed onto the adsorbent. That is, 9.1 mmol (33 mol % of the charged copper(I) chloride) of ethylene was adsorbed after 3 minutes and 12.3 mmol (44 mol % of the charged copper(I) chloride) of ethylene after 120 minutes.

Furthermore, the adsorbent of the present invention was contacted with the ethylene gas containing 0.6 mol % of water a further 5 times, and the ethylene adsorption amounts were substantially the same as those of the second and third times mentioned above.

EXAMPLE 13

The chemicals, gases, and solid adsorbent used in Example 12 were used.

The solid adsorbent prepared in the same manner as in Example 12 was charged into a 100 ml two-necked eggplant-flask. The flask was connected to a vessel containing the ethylene gas (water content=0.6 mol %) at 1 atm. The ethylene was then adsorbed at 20° C. onto the adsorbent, while the adsorbent was stirred with a magnetic stirrer.

The ethylene was rapidly adsorbed onto the adsorbent. That is, 26.0 mmol (94 mol % of the charged copper(I) chloride) of ethylene was adsorbed after 120 minutes. The adsorbed ethylene was then desorbed under 1 atm by heating the adsorbent by 10.8 mmol (39 mol % of the charged copper(I) chloride) at 85° C., and 14.5 mmol (52 mol % of the charged copper(I) chloride) at 106° C.

Thereafter, the flask was cooled from 106° C. to 20° C., while the flask was evacuated to 8 mmHg. The adsorbent was then again contacted with the ethylene gas (water content=0.6 mol %) at 20° C. under 1 atm to adsorb the ethylene by 15.5 mmol (56 mol % of the charged copper(I) chloride) after 3 minutes and 20.3 mmol (73 mol % of the charged copper(I) chloride) after 120 minutes.

EXAMPLE 14

The chemicals and gases used in Example 10 were used, except that special grade chemical toluene (manufactured by Takahashi Tokichi Shoten) was used instead of the carbon disulfide. The toluene was dehydrated with sodium metal, followed by distillation.

Into a 100 ml two-necked, eggplant-type flask, 2.46 g (18.4 mmol) of aluminum chloride, 2.74 g (27.7 mmol) of copper(I) chloride, and 3.61 g (33.2 mmol in terms of the monomer residual group) of polystyrene resin, Bio-Beads SM-2 were charged, and then 20 ml of toluene was added to the mixture. The resultant mixture was heated under reflux, while the mixture was stirred with a magnetic stirrer. The resultant mixture was then evacuated to 4 mmHg to thoroughly remove the toluene, while the mixture was stirred at 20° C. to 50° C. for 6 hours with a magnetic stirrer. Thus, a solid adsorbent was prepared.

The ethylene adsorption amounts of the adsorbent were determined in the same manner as in Example 10.

As a result, 14.7 mmol of ethylene was adsorbed onto the adsorbent after 3 minutes and 19.2 mmol after 60 minutes.

The ethylene adsorbed absorbent was heated at 106° C. under 1 atm to rapidly release the ethylene. The released amount of ethylene was 9.5 mmol after 10 minutes. As a result of gas chromatograph analysis (Porapak Q column, column temp.=60° C., column length=2 m), the released gas was found to be ethylene and no other component was detected in the released gas.

EXAMPLE 15

The chemicals and gases used in Example 10 were used, except that special grade chemical dichloromethane (manufactured by Nakarai Kagaku Yakuhin Kabushiki Kaisha) was used instead of the carbon disulfide. The dichloromethane was dehydrated with phosphorus pentoxide, followed by distillation.

Into a 100 ml two-necked, eggplant-type flask, 2.46 g (18.14 mmol) of aluminum chloride, 2.74 g (27.7 mmol) of copper(I) chloride, and 3.61 g (33.2 mmol in terms of the monomer residual group) of polystyrene resin, Bio-Beads SM-2 were charged, and then 20 ml of dichloromethane was added to the mixture. The resultant mixture was heated under reflux, while the mixture was stirred with a magnetic stirrer. The resultant mixture was then evacuated to 4 mmHg to thoroughly remove the dichloromethane, while the mixture was stirred at 20° C. to 50° C. for 6 hours with a magnetic stirrer. Thus, a solid adsorbent was prepared.

The ethylene adsorption amounts of the adsorbent were determined in the same manner as in Example 10.

As a result, 13.6 mmol of ethylene was adsorbed onto the adsorbent after 3 minutes and 19.0 mmol after 60 minutes.

The ethylene adsorbed absorbent was heated at 110° C. under 1 atm to rapidly release the ethylene. The released amount of ethylene was 9.9 mmol after 10 minutes. As a result of the gas chromatograph analysis as in Example 14, the released gas was found to be ethylene and no other component was detected in the released gas.

EXAMPLE 16

The chemicals and gases used in Example 10 were used, except that special grade chemical aluminum iodide (manufactured by Yanagishima Seiyaku Kabushiki Kaisha) was used instead of the aluminum chloride.

Into a 100 ml two-necked, eggplant-type flask, 8.2 g (20 mmol) of aluminum iodide, 2.0 g (24 mmol) of copper(I) chloride, and 2.5 g (24 mmol in terms of the monomer residual group) of polystyrene resin, Bio-Beads SM-2 were charged, and then 20 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent was prepared.

The ethylene adsorption amounts of the adsorbent were determined in the same manner as in Example 10.

As a result, 2.1 mmol of ethylene was adsorbed onto the adsorbent after 3 minutes and 3.2 mmol after 60 minutes.

The ethylene adsorbed absorbent was heated at 106° C. under 1 atm to rapidly release the ethylene. The released amount of ethylene was 1.2 mmol after 10 minutes. As a result of the gas chromatograph analysis as in Example 14, the released gas was found to be ethylene and no other component was detected in the released gas.

EXAMPLE 17

The chemicals and gases used in Example 10 were used, except that special grade chemical aluminum iodide and copper(I) iodide (both manufactured by Yanagishima Seiyaku Kabushiki Kaisha) were used instead of the aluminum chloride and copper(I) chloride, respectively.

Into a 100 ml two-necked, eggplant-type flask, 8.2 g (20 mmol) of aluminum iodide, 3.8 g (20 mmol) of copper(I) iodide, and 2.5 g (24 mmol in terms of the monomer residual group) of polystyrene resin, Bio-Beads SM-2 were charged, and then 20 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent was prepared.

The ethylene adsorption amounts of the adsorbent were determined in the same manner as in Example 10.

As a result, 3.4 mmol of ethylene was adsorbed onto the adsorbent after 3 minutes and 4.4 mmol after 60 minutes.

The ethylene adsorbed absorbent was heated at 106° C. under 1 atm to rapidly release the ethylene. The released amount of ethylene was 1.8 mmol after 10 minutes. As a result of the gas chromatograph analysis as in Example 14, the released gas was found to be ethylene and no other component was detected in the released gas.

EXAMPLE 18

The chemicals and gases used in Example 10 were used, except that crosslinked polystyrene resin "S-2001" (manufactured by Shoko Tsusho Kabushiki Kaisha, 71% styrene and 29% divinyl benzene copolymer) was used instead of the polystyrene resin, Bio-Beads SM-2.

Into a 100 ml two-necked, eggplant-type flask, 2.88 g (21.6 mmol) of aluminum chloride, 2.14 g (21.6 mmol) of copper(I) chloride, and 2.83 g (26.0 mmol in terms of the monomer residual group) of the polystyrene resin, S-2001 were charged, and then 30 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent was prepared.

The ethylene adsorption amounts of the adsorbent were determined in the same manner as in Example 10.

As a result, 19.2 mmol of ethylene was adsorbed onto the adsorbent after 3 minutes and 22.0 mmol after 60 minutes.

The ethylene adsorbed absorbent was heated at 100° C. under 1 atm to rapidly release the ethylene. The released amount of ethylene was 21.8 mmol after 10 minutes. As a result of the gas chromatograph analysis as in Example 14, the released gas was found to be ethylene and no other component was detected in the released gas.

EXAMPLE 19

The following chemicals and gases were used in this Example.

Copper(I) chloride: Special grade chemical copper(I) chloride, manufactured by Komune Kagaku Yakuhin Kabushiki Kaisha (Japan), was vacuum dried at 80° C. for 12 hours.

Carbon disulfide: First grade chemical carbon disulfide, manufactured by Yoneyama Yakuhin Kogyo Kabushiki Kaisha (Japan) was dehydrated with phosphorus pentoxide, followed by distillation.

Polystyrene resin: Bio-Beads SM-2 (copolymer beads of 80 mol % styrene and 20 mol % divinylbenzene having a size of 20 to 50 mesh manufactured by Bio-Rad Laboratories Co., Ltd.) was purified by washing the beads, while stirring, with a magnetic stirrer, in a 6N hydrochloric acid at 55° C. for 2 hours, in a 4N sodium hydroxide at 55° C. for 2 hours, in water at 55° C. for 2 hours, in methanol at 25° C. for 1 hour, in dichloromethane at 25° C. for 1 hour to remove impurities from the beads, and then vacuum dried at 80° C. for 12 hours.

Ethylene gas: A bomb gas (manufactured by Takachiho Kagaku Kabushiki Kaisha (Japan)) was used after adjusting the water content to 0.6 mol % (6000 ppm).

Into a 100 ml two-necked, eggplant-type flask, 1.49 g (15.0 mmol) of copper(I) chloride and 1.87 g (18.0 mmol in terms of the monomer residual group) of polystyrene resin, Bio-Beads SM-2, were charged under a dry nitrogen atmosphere. 20 ml of carbon disulfide was added to the mixture. The mixture was heated under reflux, while being stirred with a magnetic stirrer. Thereafter, the carbon disulfide was thoroughly removed by evacuating the flask to 4 mmHg while stirring with a magnetic stirrer at a temperature of 20° C. to 50° C. for 6 hours. Thus, a solid adsorbent in the form of pale red-brown resin particles was prepared.

The adsorbent was charged into a 100 ml two-necked, eggplant-type flask and ethylene was then adsorbed onto the adsorbent at 20° C. by connecting the flask to a vessel containing the ethylene gas (water conent=0.6 mol %) at 1 atm, while the adsorbent was stirred with a magnetic stirrer.

The ethylene was rapidly adsorbed onto the adsorbent. That is, 0.8 mmol (5 mol % of the charged copper(I) chloride) of ethylene was adsorbed after 1 minute and 1.2 mmol (8 mol % of the charged copper(I) chloride) of ethylene was adsorbed after 60 minutes.

The ethylene adsorbed adsorbent was evacuated to 4 mmHg at a temperature of 20° C. for 20 minutes to release the adsorbed ethylene from the adsorbent.

The two-necked flask was connected to a vessel containing the ethylene gas (water content=0.6 mol %) at 1 atm, while the adsorbent was stirred with a magnetic stirrer. Thus, carbon ethylene monoxide was adsorbed at 20° C.

The ethylene was rapidly adsorbed onto the adsorbent. That is, 0.8 mmol (5 mol % of the charged copper(I) chloride) of ethylene was adsorbed after 1 minute and 1.2 mmol (8 mol % of the charged copper(I) chloride) of ethylene was adsorbed after 60 minutes.

Furthermore, the adsorbent of the present invention was contacted with the ethylene gas containing 0.6 mol % of water a further five times, after desorbing the adsorbed ethylene, and the ethylene adsorption amounts were substantially the same as those of the first and second contacts mentioned above.

EXAMPLE 20

The chemicals, gases, and solid adsorbent used in Example 19 were used.

The solid adsorbent prepared in the same manner as in Example 19 was charged into a 100 ml two-necked eggplant flask. The flask was connected to a vessel containing the ethylene gas (water content=0.6 mol %) at 1 atm. Thus, the ethylene was adsorbed at 20° C. onto the adsorbent, while the adsorbent was stirred with a magnetic stirrer.

The ethylene was rapidly adsorbed onto the adsorbent. That is, 1.2 mmol (8 mol % of the charged copper(I) chloride) of ethylene was adsorbed after 60 minutes.

The ethylene adsorbed adsorbent was heated at 90° C. under 1 atm to release 1.2 mmol (8 mol % of the charged copper(I) chloride) of ethylene.

Thereafter, the flask was again connected to the vessel containing the ethylene gas (water content=0.6 mol %) at 1 atm. Thus, the ethylene was adsorbed onto the adsorbent at 20° C., while the adsorbent was stirred with a magnetic stirrer. The ethylene was rapidly adsorbed. That is, 0.8 mmol (5 mol % of the charged copper(I) chloride) of ethylene was adsorbed after 1 minute and 1.2 mmol (8 mol % of the charged copper(I) chloride) of ethylene after 60 minutes.

Furthermore, the adsorbent of the present invention was contacted with the ethylene gas containing 0.6 mol % of water a further five times, after desorbing the adsorbed ethylene, and the ethylene adsorption amounts were substantially the same as those of the first and second contacts mentioned above.

EXAMPLE 21

The chemicals and gases used in Example 19 were used, together with special grade chemical magnesium chloride (manufactured by Junsei Kagaku Yakuhin Kogyo Kabushiki Kaisha (Japan)).

Into a 100 ml two-necked, eggplant-type flask, 1.43 g (15.0 mmol) of magnesium chloride, 1.49 g (15.0 mmol) of copper(I) chloride, and 1.87 g (18.0 mmol in terms of the monomer residual group) of polystyrene resin, Bio-Beads SM-2, were charged under a dry nitrogen atmosphere. 20 ml of carbon disulfide was added to the mixture. The mixture was heated under reflux, while being stirred with a magnetic stirrer. Thereafter, the carbon disulfide was thoroughly removed by evacuating the flask to 4 mmHg, while stirring with a magnetic stirrer at 20° C. to 50° C. for 6 hours. Thus, a solid adsorbent was prepared.

The adsorbent was charged into a 100 ml two-necked eggplant flask. The flask was connected to a vessel containing the ethylene gas (water content=0.6 mol %) at 1 atm. Thus, the ethylene was adsorbed at 20° C. onto the adsorbent, while the adsorbent was stirred with a magnetic stirrer.

The ethylene was rapidly adsorbed onto the adsorbent. That is, 1.1 mmol (7 mol % of the charged copper(I) chloride) of ethylene was adsorbed after 1 minute and 1.7 mmol (11 mol % of the charged copper(I) chloride) of ethylene was adsorbed after 60 minutes.

The ethylene adsorbed adsorbent was evacuated to 4 mmHg at 20° C. for 20 minutes with a vacuum pump to release the adsorbed ethylene.

Thereafter, the flask was again connected to the vessel containing the ethylene gas (water content=0.6 mol %) at 1 atm. Thus, the ethylene was adsorbed onto the adsorbent at 20° C., while the adsorbent was stirred with a magnetic stirrer. The ethylene was rapidly adsorbed. That is, 1.1 mmol (7 mol % of the charged copper(I) chloride) of ethylene was adsorbed after 1 minute and 1.7 mmol (11 mol % of the charged copper(I) chloride) of ethylene after 60 minutes.

Furthermore, the adsorbent of the present invention was contacted with the ethylene gas containing 0.6 mol % of water a further five times, after desorbing the adsorbed ethylene, and the ethylene adsorption amounts were substantially the same as those of the first and second contacts mentioned above.

EXAMPLE 22

Propylene gas generated from special grade chemical propylene (50% xylene solution) (manufactured by Tokyo Kasei Yakuhin Kogyo Kabushiki Kaisha) was used after being purified by passing it through a packed column of activated carbon.

The solid adsorbent prepared in the same manner as in Example 19 was charged into a 100 ml two-necked eggplant flask. The flask was connected to a vessel containing the propylene gas at 1 atm. Thus, the propylene was adsorbed at 20° C. onto the adsorbent, while the adsorbent was stirred with a magnetic stirrer.

The propylene was rapidly adsorbed onto the adsorbent. That is, 2.3 mmol (15 mol % of the charged copper(I) chloride) of propylene was adsorbed after 1 minute and 5.1 mmol (34 mol % of the charged copper(I) chloride) of propylene 60 minutes.

The propylene adsorbed adsorbent was evacuated to 4 mmHg at 20° C. for 20 minutes with a vacuum pump to release the adsorbed ethylene.

Thereafter, the flask was again connected to the vessel containing the propylene gas at 1 atm. Thus, the propylene was adsorbed onto the adsorbent at 20° C., while the adsorbent was stirred with a magnetic stirrer. The propylene was rapidly adsorbed. That is, 2.3 mmol (15 mol % of the charged copper(I) chloride) of propylene was adsorbed after 1 minute and 2.3 mmol (34 mol % of the charged copper(I) chloride) of propylene after 60 minutes.

Furthermore, the adsorbent of the present invention was contacted with the propylene gas a further five times, after desorbing the adsorbed propylene, and the propylene adsorption amounts were substantially the same as those of the first and second contacts mentioned above.

EXAMPLE 23

Special grade chemical isobutene manufactured by Tokyo Kasei Kabushiki Kaisha was used.

The solid adsorbent prepared in the same manner as in Example 19 was charged into a 100 ml two-necked eggplant flask. The flask was connected to a vessel containing the isobutene gas at 1 atm. Thus, the isobutene was adsorbed at 20° C. onto the adsorbent, while the adsorbent was stirred with a magnetic stirrer.

The isobutene was rapidly adsorbed onto the adsorbent. That is, 3.5 mmol (23 mol % of the charged copper(I) chloride) of isobutene was adsorbed after 1 minute and 10.5 mmol (70 mol % of the charged copper(I) chloride) of isobutene after 60 minutes.

The isobutene adsorbed adsorbent was evacuated to 4 mmHg at 20° C. for 20 minutes with a vacuum pump to release the adsorbed isobutene.

Thereafter, the flask was again connected to the vessel containing the isobutene gas at 1 atm. Thus, the isobutene was adsorbed onto the adsorbent at 20° C., while the adsorbent was stirred with a magnetic stirrer. The isobutene was rapidly adsorbed. That is, 3.7 mmol (25 mol % of the charged copper(I) chloride) of isobutene was adsorbed after 1 minute and 10.5 mmol (70 mol % of the charged copper(I) chloride) of isobutene after 60 minutes.

Furthermore, the adsorbent of the present invention was contacted with the isobutene gas a further five times, after desorbing the adsorbed isobutene, and the isobutene adsorption amounts were substantially the same as those of the first and second contacts mentioned above.

EXAMPLE 24

The chemicals and gas used in Example 22 were used, except that special grade chemical toluene (manufactured by Tokyo Kasei Yakuhin Kogyo Kabushiki Kaisha) was used instead of the carbon disulfide. The toluene was dehydrated with sodium metal, followed by distillation.

Into a 100 ml two-necked, eggplant-type flask, 1.49 g (15.0 mmol) of copper(I) chloride, and 1.87 g (18.0 mmol in terms of the monomer residual group) of polystyrene resin, Bio-Beads SM-2 were charged, and then 20 ml of toluene was added to the mixture. The resultant mixture was heated under reflux, while the mixture was stirred with a magnetic stirrer. The resultant mixture was then evacuated to 4 mmHg to thoroughly remove the toluene, while the mixture was stirred at 20° C. to 50° C. for 6 hours with a magnetic stirrer. Thus, a solid adsorbent was prepared.

The adsorbent was charged into two-necked, eggplant type flask and the flask was then connected to a vessel containing the propylene at 1 atm. Thus, the propylene was adsorbed onto the adsorbent at 20° C., while the adsorbent was stirred with a magnetic stirrer.

As a result, the propylene was rapidly adsorbed. That is, 1.8 mmol (12 mol % of the charged copper chloride) of propylene was adsorbed after 1 minutes and 4.8 mmol (32 mol % of the charged copper(I) chloride) of propylene after 60 minutes.

EXAMPLE 25

The chemicals and gas used in Example 19 were used, except that special grade chemical copper(I) bromide (manufactured by Komune Kagaku Yakuhin Kabushiki Kaisha) was used instead of the copper(I) chloride.

Into a 100 ml two-necked, eggplant-type flask, 2.15 g (15.0 mmol) of copper(I) bromide, and 1.87 g (18.0 mmol in terms of the monomer residual group) of polystyrene resin, Bio-Beads SM-2 were charged, and then 20 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent in the form of white resin particles was prepared.

The adsorbent was charged into a two-necked, eggplant type flask and the flask was then connected to a vessel containing the ethylene gas (water content=0.6 mol %) at 1 atm. Thus, the ethylene was adsorbed onto the adsorbent at 20° C., while the adsorbent was stirred with a magnetic stirrer.

As a result, the ethylene was rapidly adsorbed. That is, 0.75 mmol (5 mol % of the charged copper(I) bromide) of ethylene was adsorbed after 1 minutes and 1.4 mmol (9 mol % of the charged copper(I) bromide) of ethylene after 60 minutes.

EXAMPLE 26

The chemicals and gas used in Example 22 were used, except that special grade chemical acetone (manufactured by Tokyo Kasei Yakuhin Kogyo Kabushiki Kaisha) was used instead of the carbon disulfide.

Into a 100 ml two-necked, eggplant-type flask, 1.49 g (15.0 mmol) of copper(I) chloride, and 1.87 g (18.0 mmol in terms of the monomer residual group) of polystyrene resin, Bio-Beads SM-2 were charged, and then 20 ml of acetone was added to the mixture. The resultant mixture was heated under reflux, while the mixture was stirred with a magnetic stirrer. The resultant mixture was then evacuated to 4 mmHg to thoroughly remove the acetone, while the mixture was stirred at 20° C. to 50° C. for 6 hours with a magnetic stirrer. Thus, a solid adsorbent in the form of white resin particles was prepared.

The adsorbent was charged into a two-necked, eggplant type flask and the flask was then connected to a vessel containing the propylene at 1 atm. Thus, the propylene was adsorbed onto the adsorbent at 20° C., while the adsorbent was stirred with a magnetic stirrer.

As a result, the propylene was rapidly adsorbed. That is, 2.0 mmol (13 mol % of the charged copper chloride) of propylene was adsorbed after 1 minutes and 5.1 mmol (34 mol % of the charged copper(I) chloride) of propylene after 60 minutes.

EXAMPLE 27

The chemicals and gas used in Example 19 were used, except that special grade chemical copper(I) iodide (manufactured by Komune Kagaku Yakuhin Kabushiki Kaisha) was used instead of the copper(I) chloride.

Into a 100 ml two-necked, eggplant-type flask, 2.86 g (15.0 mmol) of copper(I) iodide, and 1.87 g (18.0 mmol in terms of the monomer residual group) of polystyrene resin, Bio-Beads SM-2 were charged, and then 20 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 20° C. to 50° C. for 6 hours with a magnetic stirrer. Thus, a solid adsorbent was prepared.

The adsorbent was charged into a two-necked, eggplant type flask and the flask was then connected to a vessel containing the ethylene gas (water content=0.6 mol %) at 1 atm. Thus, the ethylene was adsorbed onto the adsorbent at 20° C., while the adsorbent was stirred with a magnetic stirrer.

As a result, the ethylene was rapidly adsorbed. That is, 0.6 mmol (4 mol % of the charged copper(I) iodide) of ethylene was adsorbed after 1 minute and 1.2 mmol (8 mol % of the charged copper(I) iodide) of ethylene after 60 minutes.

EXAMPLE 28

The chemicals and gas used in Example 22 were used, except that special grade chemical acetonitrile (manufactured by Tokyo Kasei Yakuhin Kogyo Kabushiki Kaisha) was used instead of the carbon disulfide.

Into a 100 ml two-necked, eggplant-type flask, 1.49 g (15.0 mmol) of copper(I) chloride, and 1.87 g (18.0 mmol in terms of the monomer residual group) of polystyrene resin, Bio-Beads SM-2 were charged, and then 20 ml of acetonitrile was added to the mixture. The resultant mixture was heated under reflux, while the mixture was stirred with a magnetic stirrer. The resultant mixture was then evacuated to 4 mmHg to thoroughly remove the acetonitrile, while the mixture was stirred at 20° C. to 50° C. for 6 hours with a magnetic stirrer. Thus, a solid adsorbent in the form of white resin particles was prepared.

The adsorbent was charged into a two-necked, eggplant type flask and the flask was then connected to a vessel containing the propylene at 1 atm. Thus, the propylene was adsorbed onto the adsorbent at 20° C., while the adsorbent was stirred with a magnetic stirrer.

As a result, the propylene was rapidly adsorbed. That is, 1.6 mmol (11 mol % of the charged copper chloride) of propylene was adsorbed after 1 minutes and 2.4 mmol (16 mol % of the charged copper(I) chloride) of propylene after 60 minutes.

EXAMPLE 29

The chemicals and gas used in Example 22 were used, except that special grade chemical cyclohexene (manufactured by Tokyo Kasei Yakuhin Kogyo Kabushiki Kaisha) was used instead of the carbon disulfide.

Into a 100 ml two-necked, eggplant-type flask, 1.49 g (15.0 mmol) of copper(I) chloride, and 1.87 g (18.0 mmol in terms of the monomer residual group) of polystyrene resin, Bio-Beads SM-2 were charged, and then 20 ml of cyclohexene was added to the mixture. The resultant mixture was heated under reflux, while the mixture was stirred with a magnetic stirrer. The resultant mixture was then evacuated to 4 mmHg to thoroughly remove the cyclohexene, while the mixture was stirred at 100° C. for 24 hours with a magnetic stirrer. Thus, a solid adsorbent in the form of white resin particles was prepared.

The adsorbent was charged into a two-necked, eggplant type flask and the flask was then connected to a vessel containing the propylene at 1 atm. Thus, the propylene was adsorbed onto the adsorbent at 20° C., while the adsorbent was stirred with a magnetic stirrer.

As a result, the propylene was rapidly adsorbed. That is, 3.8 mmol (25 mol % of the charged copper chloride) of propylene was adsorbed after 1 minute and 5.6 mmol (37 mol % of the charged copper(I) chloride) of propylene after 60 minutes.

EXAMPLE 30

The chemicals and gas used in Example 19 were used, except that crosslinked polystyrene resin "S-2001" (manufactured by Shoko Tsusho Kabushiki Kaisha, 71% styrene and 29% divinyl benzene copolymer) was used instead of the polystyrene resin, Bio-Beads SM-2.

Into a 100 ml two-necked, eggplant-type flask, 1.49 g (15.0 mmol) of copper(I) chloride, and 1.87 g (18.0 mmol in terms of the monomer residual group) of polystyrene resin, S-2001 were charged, and then 20 ml of carbon disulfide was added to the mixture. The resultant mixture was heated under reflux, while the mixture was stirred with a magnetic stirrer. The resultant mixture was then evacuated to 4 mmHg to thoroughly remove the carbon disulfide, while the mixture was stirred at 100° C. for 24 hours with a magnetic stirrer. Thus, a solid adsorbent in the form of white resin particles was prepared.

The adsorbent was charged into a two-necked, eggplant type flask and the flask was then connected to a vessel containing the ethylene gas at 1 atm. Thus, the ethylene was adsorbed onto the adsorbent at 20° C., while the adsorbent was stirred with a magentic stirrer.

As a result, the ethylene was rapidly adsorbed. That is, 0.8 mmol (5 mol % of the charged copper chloride) of ethylene was adsorbed after 1 minute and 1.1 mmol (7 mol % of the charged copper(I) chloride) of ethylene after 60 minutes.

We claim:

1. A solid adsorbent for an unsaturated hydrocarbon comprising:
   (a) (i) a silver or copper(I) halide,
   (ii) a silver or copper(I) halide and 0.1 to 10 times by mole, based on the amount of the silver or copper(I) halide, of a calcium or magnesium halide, or
   (iii) a silver or copper(I) halide and 0.1 to 10 times by mole, based on the amount of silver or copper(I) halide, of an aluminum halide, and
   (b) polystyrene having a number-average molecular weight of 5000 to 500,000 or a styrene copolymer of 40 to 99 moles of styrene and 1 to 60 moles % of divinylbenzene in an amount such that the mole ratio of a monomer residual group of the polystyrene or styrene copolymer to the silver or copper(I) halide is 0.1 to 30,
said solid adsorbent being prepared by mixing the components (a) and (b) in a solvent, followed by evaporating the solvent form the mixture.

2. A solid adsorbent as claimed in claim 1 wherein the silver halide is silver chloride, silver bromide, or silver iodide.

3. A solid adsorbent as claimed in claim 1 wherein the copper(I) halide is copper(I) chloride, copper(I) bromide, or copper(I) iodide.

4. A solid adsorbent as claimed in claim 1, wherein the calcium or magnesium halide is calcium chloride or magnesium chloride.

5. A solid adsorbent as claimed in claim 1 wherein the aluminum halides are aluminum chloride, aluminum fluoride, aluminum bromide, and aluminum iodide.

6. A solid adsorbent comprising (a)(i) or (a)(ii) and (b) as claimed in claim 1, wherein the solvent is carbon disulfide, dichloromethane, chloroform, tetrachloromethane, dichloroethane, trichloroethane, tetrachloroethane, benzene, toluene, xylene, chlorobenzene, cyclohexane, decalin, acetonitrile, propionitrile, acetone, methyl isobutyl ketone, ethyl acetate, water, an aqueous hydrogen halide solution, methanol, ethanol, or isopropanol.

7. A solid adsorbent comprising (a)(iii) and (b) as claimed in claim 1, wherein solvent is carbon disulfide, dichloromethane, chloroform, tetrachloromethane, dichloroethane, trichloroethane, tetrachloroethane, benzene, toluene, xylene, chlorobenzene, cyclohexane, or decalin.

* * * * *